United States Patent [19]
Wang

[11] Patent Number: 6,017,847
[45] Date of Patent: Jan. 25, 2000

[54] VINYL ACETATE CATALYST PREPARED WITH POTASSIUM AURATE AND COMPRISING METALLIC PALLADIUM AND GOLD ON A CARRIER PRECOATED WITH COPPER

[75] Inventor: Tao Wang, Corpus Christi, Tex.

[73] Assignee: Celanese International Corporation, Dallas, Tex.

[21] Appl. No.: 09/088,287

[22] Filed: Jun. 2, 1998

[51] Int. Cl.[7] ............................... B01J 23/72; B01J 23/42
[52] U.S. Cl. ...................... 502/331; 502/325; 502/330; 502/339
[58] Field of Search ..................... 502/325, 330, 502/331, 339

[56] References Cited

U.S. PATENT DOCUMENTS

| | | | |
|---|---|---|---|
| 4,093,559 | 6/1978 | Fernholz et al. | 502/325 |
| 4,119,567 | 10/1978 | Bartsch | 502/325 |
| 5,179,057 | 1/1993 | Bartley | 502/170 |
| 5,314,858 | 5/1994 | Colling | 502/330 |
| 5,332,710 | 7/1994 | Nicolau et al. | 502/243 |
| 5,347,046 | 9/1994 | White et al. | 560/245 |
| 5,693,586 | 12/1997 | Nicolau et al. | 502/330 |
| 5,700,753 | 12/1997 | Wang et al. | 502/330 |
| 5,731,457 | 3/1998 | Nicolau et al. | 560/245 |

FOREIGN PATENT DOCUMENTS 1188777  4/1967  United Kingdom.

OTHER PUBLICATIONS

Journal of The American Chemical Society, 1927, vol. 49, p. 1221–1226, no month available.

*Primary Examiner*—Elizabeth D. Wood
*Attorney, Agent, or Firm*—M. Susan Spiering

[57] ABSTRACT

A catalyst for the production of vinyl acetate by reaction of ethylene, oxygen and acetic acid, comprising a porous support on the porous surfaces of which is deposited catalytically effective amounts of metallic copper, palladium and gold. The catalyst is prepared by steps comprising precoating the support with a water-insoluble form of copper, forming on the precoated support a water-insoluble palladium compound, reducing the palladium compound, and, if not previously reduced, the water-insoluble form of copper, to a catalytically effective amount of the free metal, impregnating the copper and palladium containing support with a solution of potassium aurate, and reducing the potassium aurate to a catalytically effective amount of metallic gold. The inventive process results in a catalyst wherein the Pd, Cu, and Au form a shell metal distribution on the catalyst support.

11 Claims, No Drawings

VINYL ACETATE CATALYST PREPARED WITH POTASSIUM AURATE AND COMPRISING METALLIC PALLADIUM AND GOLD ON A CARRIER PRECOATED WITH COPPER

BACKGROUND OF THE INVENTION

1. Field of the Invention

This invention relates to new and improved catalysts for the production of vinyl acetate (VA) by reaction of ethylene, oxygen and acetic acid.

2. Background Information Including Description of Related Art

It is known to produce vinyl acetate by reaction of ethylene, oxygen and acetic acid using a catalyst consisting of metallic palladium, gold and copper supported on a carrier (for example, see U.S. Pat. No. 5,347,046 and U.S. Pat. No. 5,731,457). While the process utilizing such a catalyst is capable of producing vinyl acetate at fair levels of productivity, any expedient capable of achieving even greater productivity over the life of the catalyst is obviously advantageous.

More particularly the foregoing catalysts comprising metallic palladium, gold and copper may be prepared by a process including the steps of impregnating a porous support with a single aqueous solution or separate solutions of water-soluble salts of these metals, reacting the impregnated water-soluble salts with an appropriate alkaline compound e.g., sodium hydroxide, to "fix" the metals as water-insoluble compounds, e.g. the hydroxides, and reducing the water insoluble compounds, e.g., with ethylene or hydrazine, to convert the metals to free metallic form. This type of process has the disadvantage of requiring several steps, sometimes including at least two "fixing" steps.

The following references may be considered material to the invention claimed herein. U.S. Pat. No. 5,332,710, issued Jul. 26, 1994, to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution to precipitate such compounds, and subsequently reducing the compounds to free metallic form.

U.S. Pat. No. 5,347,046, issued Sep. 13, 1994 to White et al., discloses catalysts for the production of vinyl acetate by reaction of ethylene, oxygen, and acetic acid, comprising a palladium group metal and/or a compound thereof, gold and/or a compound thereof, and copper, nickel, cobalt, iron, manganese, lead or silver, or a compound thereof, preferably deposited on a support material.

British Patent No. 1,188,777, published Apr. 22, 1970 discloses a process for the simultaneous production of an unsaturated carboxylic acid ester, e.g. vinyl acetate, from an olefin, carboxylic acid, and oxygen, and the corresponding carboxylic acid, e.g., acetic acid, from its aldehyde, using a single supported catalyst containing a palladium compound, e.g. an oxide or salt, with one or more compounds of any of various metals, e.g. metallic gold or a gold compound such as potassium aurate.

U.S. Pat. No. 5,700,753 discloses vinyl acetate (VA) catalyst prepared by adding organometallic gold complexes to prereduced palladium catalyst prepared from $Na_2PdCl_4$. The organometallic gold compound does not require a fixing procedure.

U.S. Pat. No. 5,731,457 describes a VA catalyst prepared with non-halogen containing copper compound.

SUMMARY OF THE INVENTION

In accordance with this invention, a catalyst is provided useful for the production of vinyl acetate by reaction of ethylene, oxygen and acetic acid with low carbon dioxide selectivity, said catalyst comprising catalytically effective amounts of metallic copper, palladium and gold deposited on a support and prepared by steps comprising precoating the porous support with a catalytically effective amount of a water-insoluble form of copper, forming on the precoated support a water-insoluble palladium compound, reducing the palladium compound and, if not previously reduced, the water-insoluble form of copper to the free metals, impregnating the copper and palladium containing support with a solution of potassium aurate ($KAuO_2$) and reducing the potassium aurate to a catalytically effective amount of metallic gold. The use of such catalyst often results in lower carbon dioxide selectivity, which is usually accompanied by a higher vinyl acetate productivity, than when various conventional catalysts comprising metallic palladium and gold are employed.

Alternatively, the gold may first be placed on the precoated Cu support, followed by impregnation of the support with palladium. A further alternative embodiment involves use of sodium-free reagents as described in U.S. Pat. No. 5,693,586.

DETAILED DESCRIPTION OF THE INVENTION

Disclosed herein is a process to prepare catalyst useful in the production of VA.

Prereduced Pd/Au catalyst were prepared by the impregnation of a support with aqueous solution of $CuCl_2$ followed by fixing with NaOH. The precoated Cu catalyst was then impregnated with a Pd solution, followed by fixing with NaOH and then reduced. A thin shell of Pd and Cu catalyst was obtained, to which was then contacted with a solution of aqueous $KAuO_2$ to form a second shell of Au on the support. Ultimately, a shell catalyst of Pd and Au was formed wherein a fixing step for the Au was not necessary. The Pd and Au were distributed as a thin metal shell at or near the surface of the support structure. It has been found that generally when Cu is added to a Pd/Au catalyst, $CO_2$ selectivity decreases.

While the presence of copper on the support in a zone largely covered by metallic palladium and gold contributes to a reduction in the $CO_2$ selectivity of the catalyst, it has also been found that the deposition of the gold on the support as a solution of potassium aurate ($KAuO_2$) after the palladium has been separately deposited and reduced, followed by reduction of the potassium aurate to metallic gold, may contribute further to such $CO_2$ selectivity reduction and may also contribute to a rise in activity. Each of these reductions in carbon dioxide selectivity and a rise in catalyst activity may result in an increase in vinyl acetate productivity.

The catalyst support material is composed of particles having any of various regular or irregular shapes, such as spheres, tablets, cylinders, rings, stars, or other shapes, and may have dimensions such as diameter, length or width of about 1 to about 10 mm., preferably about 3 to 9 mm. Spheres having a diameter of about 4 to about 8 mm. are preferred. The support material may be composed of any suitable porous substance, e.g., silica, alumina, silica-alumina, titania, zirconia, silicates, aluminosilicates, titanates, spinel, silicon carbide, carbon, and the like.

The support material may have a density in the range, for example, of about 0.3 to about 1.2 g/ml, an absorptivity in the range, for example, of about 0.3 to 1.5 g $H_2O$/g support, a surface area in the range, for example, of about 10 to about 350, preferably about 100 to about 200 $m^2$/g, an average pore size in the range, for example, of about 50 to about 2000 angstroms, and a pore volume in the range, for example, of about 0.1 to about 2, preferably about 0.4 to about 1.2 ml/g.

In the preparation of the catalyst used in the process of this invention, the support material is first impregnated with an aqueous solution of a water-soluble copper salt, e.g. cupric chloride, anhydrous or dihydrate, cupric nitrate trihydrate, cupric acetate, cupric sulfate, or cupric bromide and the like. Impregnation techniques known in the art may be employed to impregnate the copper salt. Preferably, the impregnation can be accomplished by the "incipient wetness" method wherein an amount of copper compound solution used for the impregnation is from about 95 to about 100 percent of the absorptive capacity of the support material. The concentration of the solution is such that the amount of elemental copper in the impregnated solution is equal to a predetermined amount within the range, for example, of about 0.3 to about 5.0, preferably about 0.5 to about 3.0 g/l of catalyst.

Following impregnation of the support with an aqueous solution of copper compound the copper is "fixed," i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkali metal in the alkaline compound should be in an amount, for example, about 1 to about 2, preferably about 1.1 to about 1.6 moles per mole of anion present in the soluble copper salt. The fixing of the copper may be done by techniques known in the art. Preferably, however, fixing of the copper is accomplished by the incipient wetness method wherein the impregnated support is dried, e.g., at a temperature of 150° C. for one hour, contacted with an amount of solution of the alkaline material equal to about 95–100% of the pore volume of the support, and allowed to stand for a period of about ½ hour to about 16 hours; or the roto-immersion method wherein the impregnated support without drying is immersed in a solution of the alkaline material and is rotated and/or tumbled during at least the initial period of precipitation such that a thin band of the precipitated copper compound is formed at or near the surface of the support particles. The rotation and tumbling may be carried out, for example, at about 1 to about 10 rpm for a period of about 0.5 to about 4 hours. The contemplated roto-immersion method is disclosed in U.S. Pat. No. 5,332,710, the entire disclosure of which is incorporated by reference.

Optionally, the support containing the fixed copper compound may be washed until there is essentially no trace of anions, e.g., halides in the catalyst, dried, e.g., in a fluidized bed drier at 100° C. for one hour, calcined, e.g., by heating in air at 200° C. or 18 hours, and reduced, for example, in the vapor phase by contacting the copper-containing support with a gaseous hydrocarbon such as ethylene (5% in nitrogen), e.g., at 150° C. for 5 hours, or in the liquid phase by contacting the support before washing and drying with an aqueous solution of hydrazine hydrate containing an excess molar ratio of hydrazine to copper of, for example, about 8:1 to 12:1, at room temperature, for about 0.5 to about 3 hours, after which the support is washed and dried as described. Although any of the foregoing optional steps may be carried out singly or in combination to accomplish any desired purpose, such steps may not be necessary since the washing, drying and particularly the reduction of the copper compound can often be adequately accomplished by the similar steps carried out on the palladium compound with which the copper containing support material is subsequently impregnated, as more finally described hereinafter.

The support material containing a zone of fixed insoluble copper compound, e.g., cupric hydroxide, or free copper metal with possibly some oxide, is then treated to deposit a catalytically effective amount of palladium on the porous surfaces of the support particles by techniques similar to those described previously for the deposition of copper, Thus, the support which has been precoated with copper as described may be impregnated with an aqueous solution of a water-soluble compound of palladium. Palladium(II) chloride, sodium palladium(II) chloride (i.e., sodium tetrachloropalladium(II), $Na_2PdCl_4$), potassium palladium (II) chloride, palladium(II) nitrate or palladium(II) sulfate are examples of suitable water-soluble palladium compounds. Sodium tetrachloropalladium(II) is the preferred salt for impregnation because of its good water solubility. The impregnation can be accomplished as described for copper, preferably by incipient wetness, and the concentration of the solution is such that the amount of elemental palladium in the solution absorbed on the support is equal to a desired predetermined amount. The impregnation is such as to provide, for example, about 1 to about 10 g of elemental palladium per liter of finished catalyst.

After the impregnation of the support with an aqueous solution of water-soluble salt of palladium, the palladium is fixed, i.e., precipitated, as a water-insoluble compound such as the hydroxide, by reaction with an appropriate alkaline compound, e.g., an alkali metal hydroxide, as described for copper, preferably by incipient wetness or roto-immersion.

The fixed palladium compound, and copper compound, if not previously reduced, are then reduced, e.g., in the vapor phase with ethylene, after first washing and drying the catalyst containing the fixed palladium compound and copper compound if not previously reduced, or in the liquid phase at room temperature with an aqueous solution of hydrazine hydrate followed by washing and drying, both as described previously for copper. The reduction of the fixed palladium and copper compounds mainly results in the formation of the free metals, although a minor amount of metal oxides may also be present.

After the catalyst containing palladium in free metallic form deposited on the copper precoated support material is prepared by any of the foregoing methods, it is impregnated with an aqueous solution of potassium aurate, preferably by incipient wetness. The catalyst is then dried such that the catalyst contains potassium aurate in an amount sufficient to provide, for example, about 0.5 to about 10 g of elemental gold per liter of finished catalyst, with the amount of gold being from about 10 to about 125 wt. % based on the weight of palladium present. The potassium aurate is then reduced to metallic gold using any of the techniques described previously for the reduction of palladium from the fixed, i.e., water insoluble, palladium compound on the surface of the support. Such reduction of potassium aurate is carried out without any necessity for the intermediate steps of fixing the gold on the support as a water-insoluble compound and washing such compound until chlorine-free, as described previously for copper and palladium and as ordinarily required for gold in the preparation of vinyl acetate catalysts comprising palladium and gold. The elimination of such fixing and washing steps in connection with gold is an important advantage in the preparation of the catalyst of this invention.

Although the catalysts of this invention have been described primarily in connection with those containing only palladium, gold, and copper as catalytically active metals, the catalyst may also contain one or more additional catalytically active metallic elements in the form of the free metal, oxide, or mixture of free metal and oxide. Such metallic elements may be, for example, magnesium, calcium, barium, zirconium and/or cerium. When a metal in addition to palladium, gold, and copper is desired in the catalyst, the support may usually be impregnated with a water soluble salt of such metal dissolved in the same impregnating solution as that containing the water-soluble palladium salt. The support may thus be simultaneously impregnated with water-soluble salts of palladium and the additional metal which are then simultaneously fixed and reduced in the same manner as described previously for palladium and copper. The catalyst containing the copper and palladium as the free metals and an additional metal as the oxide and/or free metal is then impregnated with potassium aurate which is then reduced to gold as free metal without an intermediate fixing step as described previously in connection with copper and palladium as the only other metals in addition to gold.

One of the problems in producing VA catalysts has been low noble metal retention on the catalyst support. The use of $KAuO_2$ precursors offer a method to produce salt free highly dispersed metallic particles with no fixing step involved for the Au complexes. An advantage of no fixing step for the Au complexes is the increased gold retention since Au is partially washed out of the catalyst during fixing/washing step under prior art techniques. A high gold metal retention catalyst was obtained by this method. The catalyst also contains Cu, Pd and Au distributed in a thin shell at or near the surface of the catalyst support.

Advantageously, the catalyst containing palladium and gold in free metallic form deposited on a support which has been precoated with copper may optionally be impregnated with a solution of an alkali metal acetate, preferably potassium or sodium acetate, and most preferably potassium acetate. After drying, the finished catalyst may contain, for example, about 10 to about 70, preferably about 20 to about 60 g of alkali metal acetate per liter of finished catalyst.

When vinyl acetate is prepared using the catalyst of the present invention, a stream of gas, which contains ethylene, oxygen or air, acetic acid, and desirably an alkali metal acetate, is passed over the catalyst. The composition of the gas stream can be varied within wide limits, taking in account explosive limits. For example, the molar ratio of ethylene to oxygen can be about 80:20 to about 98:2, the molar ratio of acetic acid to ethylene can be about 2:1 to about 1:10, preferably about 1:2 to 1:5, and the content of gaseous alkali metal acetate can be about 1 to about 100 ppm based on the weight of acetic acid employed. The gas stream also can contain other inert gases, such as nitrogen, carbon dioxide and/or saturated hydrocarbons. Reaction temperatures which can be used are elevated temperatures, preferably those in the range of about 150–220° C. The pressure employed can be a somewhat reduced pressure, normal pressure or elevated pressure, preferably a pressure of up to about 20 atmospheres gauge.

As an alternate embodiment of the invention, sodium-free reagents may be employed. For example, the potassium salts of palladium and hydroxide precipitating solutions may be employed. See U.S. Pat. No. 5,693,586.

A further alternative involves the simultaneous impregnation of the activating compound with the aurate complex. For example potassium aurate and potassium acetate may be placed in one step onto the supported Pd/Cu catalyst.

Another alternative embodiment involves the preparation of the catalyst wherein the aurate is added to the Cu coated support followed by impregnation of the Pd compound onto the support.

The following examples further illustrate the invention.

EXAMPLES 1 to 4

These examples illustrate the preparation of catalysts under this invention containing varying amounts of palladium and gold in free metallic form.

In Example 1, a support material precoated with a water-insoluble form of copper and containing prereduced palladium metal was prepared as follows:

An unmodified support material in an amount of 250 ml consisting of Sud Chemie KA-160 silica spheres having a nominal diameter of 7 mm., a density of about 0.562 g/ml, and absorptivity of about 0.583 g $H_2O$/g support, a surface area of about 160 to 175 $m^2$/g, and a pore volume of about 0.68 ml/g., was first impregnated by incipient wetness with 82.5 ml of an aqueous solution of cupric chloride sufficient to provide about 1.9 g of elemental copper per liter of catalyst. The support was shaken in the solution for 5 minutes to ensure complete absorption of the solution. The copper was then fixed to the support as cupric hydroxide by contacting the treated support by roto-immersion for 2.5 hours at approximately 5 rpm with 283 ml of an aqueous sodium hydroxide solution prepared from 50% w/w NaOH/$H_2O$ in an amount of 120% of that needed to convert the copper to its hydroxide. The solution was drained from the treated support which was then washed with deionized water until chloride free (about 5 hours) and dried overnight at 150° C. under constant nitrogen purge.

The support precoated with water-insoluble cupric hydroxide was then impregnated by incipient wetness with 82.5 ml of an aqueous solution of sodium tetrachloropalladium(II), $Na_2PdCl_4$, sufficient to provide about 7 g of elemental palladium per liter of catalyst, and the support was subjected to the steps of shaking to ensure complete absorption of the solution, fixing of the palladium as its hydroxide by roto-immersion in aqueous NaOH solution, draining of the NaOH solution, and washing and drying of the support, using the same procedures as described previously for the coating of the support with cupric hydroxide. The copper and palladium were then reduced to the free metals by contacting the support with ethylene (5% in nitrogen) in the vapor phase at 150° C. for 5 hours, to obtain a support containing nominal amounts of 1.9 g/l of copper and 7 g/l of prereduced palladium.

In the production of potassium aurate utilized to impregnate the support with gold, auric hydroxide, Au(OH)$_3$ was first prepared by mixing 300 g of sodium tetrachlorogold (III), NaAuCl$_4$, containing 0.20 g Au/g solution with 73.6 g of a 50% w/w NaOH/$H_2O$ dissolved in 200 ml deionized water. An excess of NaOH was added to bring the pH to about 8 and the solution was stirred and heated to 60° C. for 3 hours to form an orange precipitate Filtration yielded on orange solid which was washed with deionized water until chloride free and dried in a vacuum oven at 50° C. in a flow of $N_2$ to obtain an orange red solid of Au(OH)$_3$.

Auric hydroxide in an amount of 0.5 gram was mixed with 0.12 gram of KOH in 35 ml of water, and the resulting orange suspension was heated to 82 to 85° C. and stirred at this temperature until all solids were dissolved to yield a clear yellow solution of potassium aurate, $KAuO_2$, in an amount containing about 0.4 gram of elemental gold. This solution was added to 100 ml of support containing nominal amounts of 1.9 g/l of precoated and prereduced copper and 7 g/l of prereduced palladium prepared as described previously using ethylene as reducing agent. The impregnation was conducted for about 25–30 min. The catalyst was dried in an oven at 100° C. for 5 hours in a flow of $N_2$ purge. The gold in the treated catalyst was then reduced by 5% ethylene in $N_2$ at 120° C. for 5 hours to obtain a catalyst containing a nominal amount of 4 g/l of free metallic gold on the support.

Finally the catalyst was impregnated by incipient wetness with an aqueous solution of 4 g of potassium acetate in 33 ml $H_2O$ and dried in a fluid bed drier at 100° C. for 1.5 hour.

In Example 2, a duplicate batch of catalyst was prepared using the procedures of Example 1.

In Example 3, the procedures of Example 1 were followed except that the amounts of materials and reagents were increased proportionately so as to obtain a batch of 6 liters of catalyst containing the same nominal amounts of copper, palladium and gold as the catalyst of Example 1.

In Example 4, the procedures of Example 1 were followed except that the amounts of reagents used to prepare the solution of potassium aurate were changed so that such solution contained 0.5 rather that 0.4 gram of elemental gold, and the finished catalyst thus contained a nominal amount of 5 rather than 4 g/l of free metallic gold.

The nominal amounts of Pd, Au, and Cu corresponding to the concentrations and amounts of impregnating solutions (Nom. Amt., g/L), and actual amounts of Pd and Au on the catalysts of Examples 1–4 determined by analysis, and metal retention are shown in Table I.

The catalysts of the examples were tested for their activity and selectivity to various by-products in the production of vinyl acetate by reaction of ethylene, oxygen and acetic acid. To accomplish this, about 60 ml of the catalyst prepared as described were placed in a stainless steel basket with the temperature capable of being measured by a thermocouple at both the top and bottom of the basket. The basket was placed in a Berty continuously stirred tank reactor of the recirculating type and was maintained at a temperature which provided about 45% oxygen conversion with an electric heating mantle. A gas mixture of about 50 normal liters (measured at N.T.P.) of ethylene, about 10 normal liters of oxygen, about 49 normal liters of nitrogen, about 50 g of acetic acid, and about 4 mg of potassium acetate, was caused to travel under pressure at about 12 atmospheres through the basket, and the catalyst was aged under these reaction conditions for at least 16 hours prior to a two hour run, after which the reaction was terminated. Analysis of the products was accomplished by on-line gas chromatographic analysis combined with off-line liquid product analysis by condensing the product stream at about 10° C. to obtain optimum analysis of the end products carbon dioxide ($CO_2$), heavy ends (HE) and ethyl acetate (EtOAc), the results of which were used to calculate the percent selectivities (Selectivity) of these materials for each example as shown in Table I. The relative activity of the reaction expressed as an activity factor (Activity) is also shown in Table I and is computer calculated in the following way: The computer program uses a series of equations that correlates the activity factor with the catalyst temperature (during the reaction), oxygen conversion, and a series of kinetic parameters for the reactions that take place during VA synthesis. More generally, the activity factor is inversely related to the temperature required to achieve constant oxygen conversion.

TABLE 1

| Example | 1 | 2 | 3 | 4 |
|---|---|---|---|---|
| Metal Content of Catalyst Nom. Amt., g/l | | | | |
| Pd | 7 | 7 | 7 | 7 |
| Au | 4 | 4 | 4 | 5 |
| Cu | 1.9 | 1.9 | 1.9 | 1.9 |
| Actual wt. %/l | | | | |
| Pd | 1.09 | 1.06 | 1.02 | 1.10 |
| Au | 0.61 | 0.66 | 0.66 | 0.70 |
| Cu | 0.25 | 0.31 | 0.27 | 0.26 |
| % metal retention | | | | |
| Pd | 97 | 93 | 90 | 96 |
| Au | 94 | 100 | 100 | 86 |
| Cu | 83 | 100 | 90 | 86 |
| Activity | 2.07 | 2.13 | 2.09 | 2.22 |
| Selectivity | | | | |
| $CO_2$ | 7.97 | 7.82 | 8.21 | 8.32 |
| HE | 1.357 | 1.325 | 1.222 | 1.515 |
| EtOAc | 0.059 | 0.058 | 0.049 | 0.061 |

The values shown in Table I indicate that the catalysts of this invention in many instances can be used to synthesize vinyl acetate by reaction of ethylene, oxygen, and acetic acid with lower $CO_2$ selectivities than various conventional and/or commercial catalysts comprising palladium and gold, while maintaining higher or equivalent levels of activity. Moreover, the use of $KAuO_2$ as the catalyst gold precursor provides more reproducible and higher levels of gold retention on the catalyst.

What is claimed is:

1. A method of preparing a catalyst for the production of vinyl acetate by reaction of ethylene oxygen and acetic acid comprising precoating a porous support with a water-insoluble form of copper, forming on the precoating support a water-insoluble palladium compound, reducing the palladium compound, and, if not previously reduced, the water-insoluble form of copper, to a catalytically effective amount of the free copper metal, impregnating said copper and palladium containing support with a solution of potassium aurate, and reducing the potassium aurate to a catalytically effective amount of metallic gold.

2. The method of claim 1 wherein said support containing metallic copper and palladium on which said potassium aurate is impregnated is prepared by steps comprising impregnating said support with an aqueous solution of a water-soluble copper salt, fixing said copper as a water-insoluble compound by reaction with an appropriate alkaline compound, impregnating said copper precoated support with an aqueous solution of a water-soluble palladium salt, fixing said palladium as a water-insoluble compound by reaction with an appropriate alkaline compound, and reducing to their free metallic state the water-insoluble compounds of copper and palladium present on the support.

3. The method of claim 2 wherein said water-soluble copper salt is cupric chloride and said water-soluble palladium salt is sodium tetrachloropalladium(II).

4. The method of claim 1 wherein said porous support contains about 0.3 to about 5.0 g of elemental copper per liter of catalyst.

5. The method of claim 1 wherein said porous support contains about 1 to about 10 g of palladium, and about 0.5 to about 10 g of gold per liter of catalyst, with the amount of gold being from about 10 to about 125 wt. % based on the weight of palladium.

6. The method of claim 1 wherein said catalyst is impregnated with a solution of an alkali metal acetate.

7. The method of claim 6 wherein said alkali metal acetate is potassium acetate which is deposited on the catalyst in an amount of about 10 to about 70 g/l of catalyst.

8. The method of claim 1 wherein the Pd, Cu, and Au form a metal shell distributed on the catalyst support.

9. The method of claim 6 wherein the aurate and acetate are added in one step.

10. The method of claim 1 prepared with sodium-free reagents.

11. The method of claim 1 wherein the aurate is added to a Cu coated support followed by impregnation of a Pd compound onto the support.

* * * * *